(12) United States Patent
Liska et al.

(10) Patent No.: US 11,518,823 B2
(45) Date of Patent: Dec. 6, 2022

(54) PHOTOINITIATORS FOR LIGHT-CURABLE COMPOSITIONS

(71) Applicant: Technische Universitaet Wien, Vienna (AT)

(72) Inventors: Robert Liska, Schleinbach (AT); Patrick Knaack, Vienna (AT); Paul Gauss, Vienna (AT); Roland Taschner, Marz (AT)

(73) Assignee: TECHNISCHE UNIVERSITAET WIEN, Vienna (AT)

( * ) Notice: Subject to any disclaimer, the term of this patent is extended or adjusted under 35 U.S.C. 154(b) by 58 days.

(21) Appl. No.: 16/633,385

(22) PCT Filed: Jul. 27, 2018

(86) PCT No.: PCT/EP2018/070464
§ 371 (c)(1),
(2) Date: Jan. 23, 2020

(87) PCT Pub. No.: WO2019/020805
PCT Pub. Date: Jan. 31, 2019

(65) Prior Publication Data
US 2020/0231531 A1 Jul. 23, 2020

(30) Foreign Application Priority Data
Jul. 27, 2017 (AT) .................................. A 313/2017

(51) Int. Cl.
| | | |
|---|---|---|
| C08F 2/50 | (2006.01) | |
| C08F 22/10 | (2006.01) | |
| C07C 69/716 | (2006.01) | |
| C07D 307/60 | (2006.01) | |
| C08F 22/20 | (2006.01) | |
| C08F 22/22 | (2006.01) | |
| C08F 222/10 | (2006.01) | |

(52) U.S. Cl.
CPC .............. C08F 2/50 (2013.01); C07C 69/716 (2013.01); C07D 307/60 (2013.01); C08F 22/1006 (2020.02); C08F 22/20 (2013.01); C08F 22/22 (2013.01); C08F 222/102 (2020.02)

(58) Field of Classification Search
CPC ..... C07C 59/19; C07C 69/716; C07C 327/20; C07C 327/02; C07D 307/60; C08F 2/50; C08F 22/1006; C08F 22/20; C08F 222/106; C08F 122/106; C08G 18/4238; C08G 18/8116; C08G 63/16
USPC .......................................................... 522/37
See application file for complete search history.

(56) References Cited

U.S. PATENT DOCUMENTS

| | | | | |
|---|---|---|---|---|
| 4,038,164 | A | 7/1977 | Via | |
| 4,234,739 | A * | 11/1980 | Photis | ..................... C07C 51/08 |
| | | | | 560/51 |
| 4,369,206 | A * | 1/1983 | Mayer | ................... C07C 59/185 |
| | | | | 204/157.71 |

FOREIGN PATENT DOCUMENTS

| | | |
|---|---|---|
| DE | 2808459 A1 | 8/1979 |
| DE | 2830953 A1 | 1/1980 |
| DE | 102010018855 A1 | 11/2011 |
| EP | 0012548 A1 | 6/1980 |

OTHER PUBLICATIONS

Search Report dated Apr. 24, 2018 in AT Application No. A3132017.
Int'l Search Report and Written Opinion dated Oct. 10, 2018 in Int'l Application No. PCT/EP2018/070464, translation of Search Report only.

(Continued)

*Primary Examiner* — Sanza L. McClendon
(74) *Attorney, Agent, or Firm* — Panitch Schhwarze Belisario & Nadel LLP

(57) ABSTRACT

Compounds of formula (I) are photoinitiators or photosensitizers in a photopolymerizable composition:

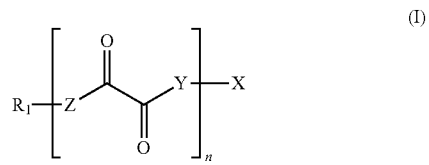

(I)

$R_1$ represents a monovalent, linear, branched or cyclic, aliphatic hydrocarbon group having 1 to 20 carbon atoms, optionally substituted with substituent(s) selected from —Cl, —Br, —OH, =O, —NH—CO—$OR_2$, —NH—CO—$R_2$ or free-radically or ionically polymerizable groups. Each $R_2$ is independently —H or $C_{1-6}$ alkyl; n is ≥1. If n=1, Z and Y are absent and X represents —$OR_3$; if n is >1, Z represents —$OR_4$—, Y represents —$OR_5$— and X represents —H or —OH. $R_3$ represents —H or $R_1$; and $R_4$ and $R_5$ each independently represent a bivalent hydrocarbon group. The polymerizable moieties as optional substituents of $R_1$ are polymerizable double or triple bonds, lactam, lactone and epoxide moieties, which are subjectable to ring-opening polymerization; and two of $R_1$ to $R_5$ may be linked to one another to form a ring or a dimer.

8 Claims, No Drawings

(56) References Cited

OTHER PUBLICATIONS

Lissi et al., "Polymerization Photosensitized by Carbonyl Compounds," Journal of Polymer Science: Polymer Chemistry Edition, vol. 17, No. 9, pp. 2791-2803 (Sep. 1979).
English Translation of International Preliminary Report on Patentability dated Jan. 28, 2020 in International Application No. PCT/EP2018/070464.

* cited by examiner

PHOTOINITIATORS FOR LIGHT-CURABLE COMPOSITIONS

CROSS-REFERENCE TO RELATED APPLICATIONS

This application is a Section 371 of International Application No. PCT/EP2018/070464, filed Jul. 27, 2018, which was published in the German language on Jan. 31, 2019 under International Publication No. WO 2019/020805 A1, which claims priority under 35 U.S.C. § 119(b) to Austrian Application No. A 313/2017, filed Jul. 27, 2017, the disclosures of which are incorporated herein by reference in their entirety.

The present invention relates to new photoinitiators for photocurable compositions.

STATE OF THE ART

In the field of photopolymerization, numerous initiators and sensitizers are known to trigger polymerization reactions, the effect of type I initiators being based on the cleavage of an intramolecular bond, while that of type II initiators is based on the abstraction and intermolecular transfer of a hydrogen atom from a co-initiator to the initiator molecule.

From the compound class of ketones, benzophenone and acetophenone as well as various derivatives thereof have been known as initiators for a long time; these include α-hydroxyalkyl phenones such as 2-hydroxy-2-methylpropiophenone, as disclosed in DE 28 08 459 A1, which used to be marketed by Ciby Geigy and is now marketed by IGM Resins under the name Darocur® 1173 and has been one of the most used initiators ever since the 1980s.

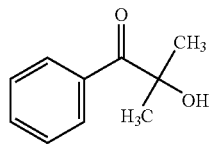

Darocur® 1173

Further initiators based on acyl and, more specifically, benzoyl groups include, for example, bisacyl derivatives of aryl phosphine oxides, as disclosed in U.S. Pat. Nos. 4,737,593 A and 4,792,632 A, and bisbenzoyl derivatives of alkyl, cycloalkyl and aryl phosphine oxides of the following formula, as disclosed in EP 615,980 A2:

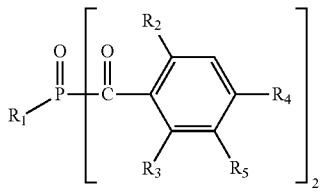

wherein $R_1$ may be a defined alkyl, cycloalkyl or aryl radical.

Moreover, glyoxylates having aromatic groups have been successfully used as photoinitiators since the middle of the 1970s. See, for example, U.S. Pat. No. 4,038,164 A, wherein initiators of the following formula are disclosed:

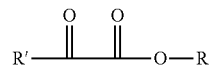

wherein R represents linear or branched-chain $C_{1-10}$ alkyl, aryl, aralkyl or a mono-, di- or trialkylsilyl group; and R' represents a heterocyclic radical, $C_{6-14}$ aryl or an optionally mono- or polysubstituted phenyl.

Recently, a new group of photoinitiators has become known from WO 2017/060459 A1 and WO 2017/060527 A1 of Dentsply Detrey GmbH; they are referred to as "compounds having an acylsilyl or acylgermyl group", although they should, in summary, be rather referred to as silyl- or germyl-substituted α-diketones or α-ketoesters or -amides and can be represented by the following formula:

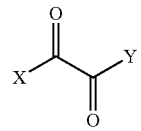

wherein X represents $R_1R_2R_3Si$— or $R_1R_2R_3Ge$—, wherein $R_1$ to $R_3$ each independently represent an optionally substituted hydrocarbon group, so that X represents a trihydrocarbylsilyl or -germyl group; and Y either represents one of the same options as mentioned for X, wherein the hydrocarbyl groups may be different from those in X, or represents —Z—$R_4$, wherein Z represents a chemical bond, —O— or —NR'—, wherein R' is an optionally substituted hydro-carbyl radical, and $R_4$ represents an optionally substituted hydrocarbyl radical or a trihydrocarbylsilyl group, wherein one or two of the hydrocarbyl radicals on the silicon atom may also be hydrocarbylcarbonyl radicals.

In any case, it is essential that the silicon or germanium atom being substituted with three (optionally further substituted) hydrocarbon radicals is in the a position to the keto group of the α-diketone or the α-ketoester or -amide. As preferred embodiments of the silicon- and/or germanium-containing initiators, various acetophenone derivatives wherein the a carbon atom has been replaced by Si or Ge are predominantly disclosed.

Such photoinitiators are said to be particularly suitable, among other purposes, for curing dental material in a patient's mouth, as they show a high quantum yield of light absorption and are said not to migrate out of the uncured mass. Moreover, acid resistance, good solubility in the polymerizable composition, thermostability and storage stability are demanded.

According to WO 2017/060459 A1 and WO 2017/060527 A1, such initiators are preferably or even obligatorily, respectively, used in combination with a co-initiator; as zo such are disclosed electron donors, e.g. amines, in the first case and particular acrylates in the second case. The thus achieved advantages include a high polymerization efficiency and curing speed and no discoloration during curing.

A disadvantage of these initiators, however, is that they are all sensitive to visible light. Moreover, the use of these photoinitiators having aromatic groups in the areas of medicine and food is restriced.

Against this backdrop, the aim of the present invention was to provide alternative photoinitiators based on α-ketoesters that are able to solve at least some of the above problems.

DISCLOSURE OF THE INVENTION

The present invention achieves the above aim by providing a novel use of compounds—more specifically α-ketoesters—of the following formula (I) as photoinitiators or photosensitizers in a photopolymerizable composition:

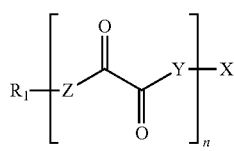
(I)

wherein $R_1$ represents a monovalent, linear, branched or cyclic, aliphatic hydrocarbon group having 1 to 20 carbon atoms, which is optionally substituted with one or more substituents selected from —Cl, —Br, —OH, =O—NH—CO—OR$_2$, —NH—CO—R$_2$ or free-radically or ionically polymerizable groups, wherein each $R_2$ radical is independently selected from —H or $C_{1-6}$ alkyl;

n is ≥1, wherein
  i) if n=1, Z and Y are not present and X represents —OR$_3$, and
  ii) if n is >1, Z represents —OR$_4$—, Y represents —OR$_6$— and X represents —H or —OH; wherein $R_3$ represents —H or one of the options mentioned for $R_1$, and
  $R_4$ and $R_5$ each independently represent a bivalent hydrocarbon group for which otherwise the same options as mentioned for $R_1$ apply;

wherein the polymerizable moieties as optional substituents of $R_1$ are selected from polymerizable double or triple bonds as well as lactam, lactone and epoxide moieties, which are subjectable to ring-opening polymerization;

and wherein any two of $R_1$ to $R_5$ may be optionally linked to one another to form a ring or a dimer.

When using the above compounds of formula (I) as photoinitiators according to the invention, they are usually at least equivalent to known initiators, both to standard initiators such as benzophenone and to relatively new compounds according to WO 2017/060459 A1 and WO 2017/060527 A1, in many cases even exceeding them, though.

Due to the lack of aromatic radicals and adjacent Si or Ge atoms, the α-ketoesters used according to the invention are physiologically harmless and do not tend to disintegrate when exposed to visible light. The compounds of formula (I) are thus ideally suited for use as photoinitiators and photosensitizers, as clearly demonstrated by the Examples below.

In preferred embodiments of the present invention, $R_1$ represents a linear, branched or cyclic aliphatic hydrocarbon group having 1 to 20 carbon atoms, in which one or more carbon atoms may have been replaced by oxygen atoms and which is optionally substituted with one or more substituents selected from —Cl, —Br, —OH and —SH; and/or n is 1 and X represents —OR$_3$, wherein $R_3$ independently represents —H or one of the options mentioned for $R_1$.

"A dimer of a compound of formula (I)" designates a compound that is formed by a formal coupling of any of the radicals $R_1$ to $R_4$ of a compound of formula (I) to any of the radicals $R_1$ to $R_4$ of an identical or a different compound of formula (I). There are, for example, three options when compounds of formula (I) in which n is 1 and X is —OR$_3$ are coupled at their terminals: via the two radicals $R_1$, via one radical $R_3$ of each of the two moieties X or via one radical $R_1$ and one radical $R_3$ of a moiety X, as represented below:

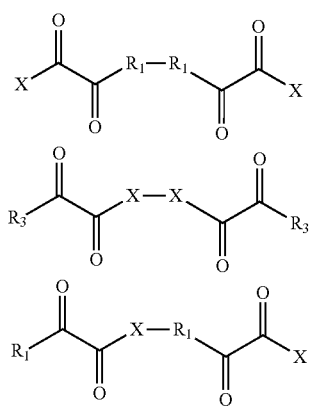

In an essentially analogous manner, two molecules of formula (I) wherein at least one of the radicals $R_1$ and $R_3$ (if n is 1) or $R_4$ (if n is >1) comprises a $O_{1-6}$ alkyl group as the radical $R_2$, i.e., if —NR$_2$— as a substitute for a carbon atom or a substituent —NH—CO—OR$_2$ or —NH—CO—R$_2$ is present, may be coupled via these radicals $R_2$—be it that either two radicals $R_2$ are coupled to one another or one radical $R_2$ is coupled to a $R_1$, $R_3$ or $R_4$ radical of the other molecule. Couplings between one $R_1$ radical and one $R_3$ or $R_4$ radical or between two $R_3$ or $R_4$ radicals are also included in the scope of the invention.

This applies in a similar manner for an optional intramolecular cyclization between any two of the radicals $R_1$ to $R_3$ (if n is 1) or $R_4$ (if n is >1) of the same molecule. Below, a terminal coupling for a case where n is 1 between $R_1$ and the radical $R_3$ (or a radical $R_2$ included therein) of the moiety X via an intermediate pentylene group that can be considered as a part of either radical $R_1$ or radical $R_3$ (or $R_2$) of the moiety X is illustrated as an example.

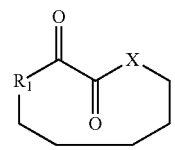

In addition to the above described preferred embodiments of the α-ketoesters of the invention, wherein n is 1, Z and Y are not present and X represents —OR$_3$, so that $R_1$ and X are each directly bound to one of the two C=O moieties, special embodiments wherein n is >1, Z represents —OR$_4$, Y represents —OR$_6$— and X represents —H or —OH are also preferred. As a result, these are oligomers or polymers of glyoxylic acid esters wherein the photoactive glyoxylic acid motif is contained n times. Particularly preferred embodiments are those wherein the carbon atom of radical $R_4$ of the moiety Z, which is adjacent to the oxygen atom is substituted with an oxo group =O, which results in a carboxyl group, and wherein X represents —OH. Thus, such molecules are polyesters which are comparably easily accessible via a polycondensation of α-ketodicarboxylic acids with diols, which is why embodiments wherein $R_1$ comprises a terminal OH group, as generally represented below, are particularly preferred:

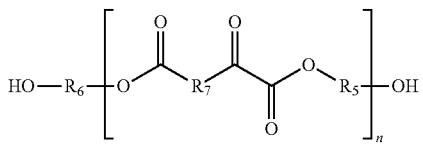

Therein, HO—$R_6$— represents the radical $R_1$— and —(C=O)—$R_7$— represents the radical —$R_4$— in formula (I), while X is —OH. The radicals $R_4$ and $R_7$ thus define the dicarboxylic acid, while the radical $R_5$ defines the diol from which such polymers are obtainable. If radical $R_7$ is —$(CH_2)_2$—, for example, this will result in α-ketoglutaric acid as the starting material for the polycondensation reaction while, if both radicals $R_5$ and $R_6$ are —$(CH_2)6$—, hexanediol will be the starting material, as this will be disclosed in the Examples later on.

The value of n defines the chain length of the compounds of formula (I) and is generally not particularly limited as long as the products are effective as photoinitiators or photosensitizers in the inventive manner. As a plurality of free radical centers are formed at the same time when such polymers of formula (I) are irradiated, such photoinitiators or photosensitizers provide for particularly rapid polymerization reactions. For the reason of an easier handling, according to the present invention, the value of n is preferably limited to 100, more preferably to 50, In some cases, significantly lower values, e.g., ranging from 2 to 10, may be preferred, too.

Those skilled in the art will understand that the compounds of formula (I) may not only be linked to one another to form dimers, but may also be bound to other molecules. Terminal OH groups, as contained in the above-described preferred embodiments of the invention that use polyesters of formula (I), are particularly easily accessible in standard derivatization reactions and may, for example, be bound easily to pre-polymers and other polymer elements in the formulations in which they are to be used as initiators or sensitizers or may also be immobilized onto solid phases. Forming alcoholates, preferably with alkali metal cations such as Li+, Na+or K+, may also prove advantageous in certain circumstances. Moreover, it is clear that some of the oxygen atoms contained in the compounds of formula (I) may be replaced by sulfur atoms, as long as this does not result in a loss of the molecules' reactivity as photoinitiators or photosensitizers.

According to the present invention, the compound of formula (I) may be used as both type I photoinitiator and type II photoinitiator, i.e., depending on the reaction conditions, an intramolecular bond may be cleaved or a hydrogen atom may be abstracted from a solvent or co-initiator molecule and transferred to the initiator of formula (I), as demonstrated later on in the exemplary embodiments.

For this reason, in preferred embodiments of the present invention, particularly in those where it serves as a type II photoinitiator, the compound of formula (I) is used in combination with one or more co-initiators in the photopolymerizable compositions.

As the co-initiators, one or more compounds selected from mono- or polyhydric alcohols (—OH), thiols (—SH), amines (—NR—), silanes (=SiH—), germanes (=GeH—), phosphines (—PRR'R"—), ethers (>CH—O—CH<), iodonium (—I+—) and sulfonium (=S+—) salts and derivatives thereof are preferably used, since such compounds proved their worth as co-initiators in the past.

Even more preferably, one or more compounds selected from sugar based polyols, glycerol or the like, thiols, polyethylene glycol or polypropylene glycol are used as co-initiators, glycerol being most preferably used as a polyhydric alcohol, which proved particularly useful as a co-initiator for compounds of formula (I) in the exemplary embodiments.

The compound of formula (I) is preferably used in an amount of 0.1 to 10 parts by weight, more preferably 0.5 to 5 parts by weight, most preferably approx. 1 to 2 parts by weight, per 100 parts by weight of polymerizable monomers in the composition.

Additionally, the compound of formula (I) is preferably used for curing free-radically polymerizable monomers such as acrylates, methacrylates, maleinimides, styrene derivatives, vinyl esters, vinyl carbonates, vinyl carbamates, and the like, as well as ring-opening monomers such as vinyl cyclopropanes, vinyl cyclooxiranes, vinyl cyclobutanes, ketene acetals, vinyl spiroesters, and the like, even more preferably for curing acrylate and methacrylate monomers, since they have proved clearly superior to standard initiators in such compositions.

As they are physiologically harmless, the compounds of formula (I) may additionally be preferably used as initiators in compositions to be cured inside the human body or for curable compositions in the food sector. This distinguishes them from the majority of standard initiators.

Further components of the polymerizable compositions are not particularly limited as long as they do not have any negative impact on the initiators' efficiency and the curing process. Any suitable fillers, solvents, further initiators or sensitizers, plasticizers, flow enhancers and the like may thus also be used, for example.

A second aspect of the present invention thus relates to a photopolymerizable composition which is characterized in that it comprises at least one compound of formula (I) as a photoinitiator or photosensitizer, at least one photopolymerizable monomer, optionally at least one co-initiator, and optionally further components as defined above.

EXAMPLES

The present invention will now be described in more detail with reference to representative examples that only serve the purpose of illustrating the invention without limiting its scope.

Materials and Procedures

If not stated otherwise below, all reagents and photoinitiators were obtained from commercial sources and used without further purification. $^1H$ NMR and $^{13}C$ NMR spectra were mostly recorded using a Bruker DPX-200 Fourier Transform spectrometer at 200 MHz or 50 MHz, respectively, and some measurements were carried out using a Bruker Avance at 400 MHz ($^1H$) and 100 MHz ($^{13}0$). Mass spectra were recorded using a Thermo Fisher Scientific ITQ 1100 and a silica capillary column (30 m×0.25 mm).

The following photoinitiators of formula (I) were tested in the Examples of the present invention:

2-Oxopropanoic Acid Ethyl Ester (Pyruvic Acid Ethyl Ester, Ethyl Pyruvate) (1)

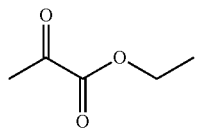

2-oxobutanoic Acid Methyl Ester (2-oxobutyric Acid Methyl Ester) (2)

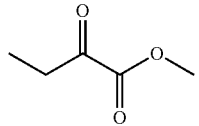

2-oxo-3-Methylbutanoic Acid Ethyl Ester (2-oxoisovaleric Acid Ethyl Ester) (3)

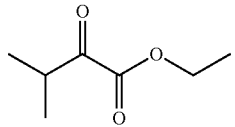

2-oxo-3,3-dimethylbutanoic Acid Methyl Ester (4)

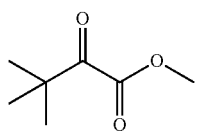

3-bromo-3-methyl-2-oxobutanoic Acid Ethyl Ester (5)

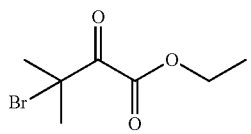

3-hydroxy-3-methyl-2-oxobutanoic Acid Ethyl Ester (6)

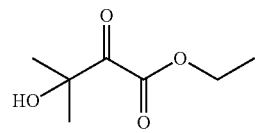

N,N'-dimethylaminopyruvate (7)

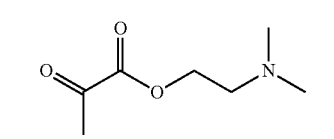

4,4-dimethyldihydrofuran-2,3-dione (8)

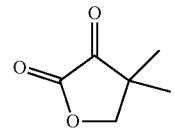

α-Ketoglutaric Acid Diethyl Ester (9)

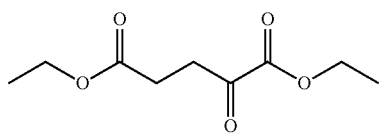

N,N'-dimethylaminopyruvate (10)

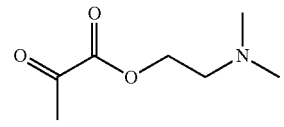

α-Ketoglutaric Acid di(hydroxyethylmethacrylate) Ester (11)

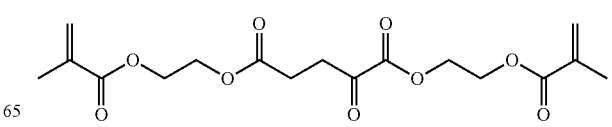

α-Ketoglutaric Acid-Hexanediol Polyester (Mn ~10000 Da) (12)

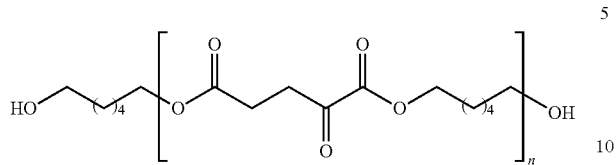

Urethane Methacrylate-Terminated α-Ketoglutaric Acid-Hexanediol Polyester (13)

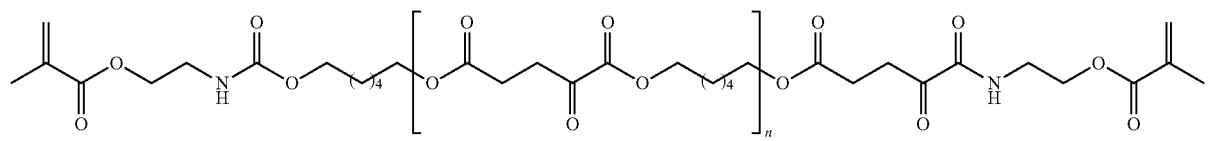

The initiators (1) to (4) were obtained from commercial sources, while the novel initiators (5) to (13) were synthesized by the inventors, as described in more detail in the Synthesis Examples later on.

In the Comparative Examples, the following four known, commercially available initiators were tested:

Benzophenone (BP)

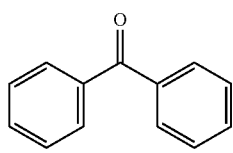

(BP)

Ethyl Phenylglyoxylate (PGO)

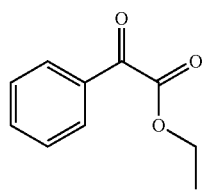

(PGO)

2-bromo-2-methyl-1-phenylpropan-1-one (2-bromoisobutyrophenone) ("Bromo Darocure", BD)

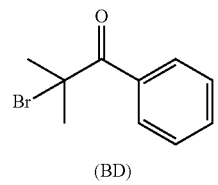

(BD)

3-(4-benzoylphenoxy)-2-hydroxy-N,N-dimethylpropane-1-amine Hydrochloride (BPQ)

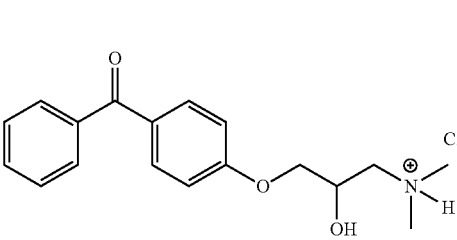

(BPQ)

Synthesis Example 1

Synthesis of 3-bromo-3-methyl-2-oxobutanoic Acid Ethyl Ester (5)

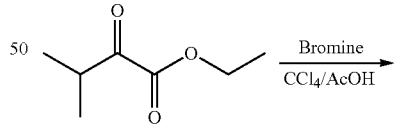

(5)

Into a 50 ml three-necked flask, 15 ml of $CCl_4$ were placed. Thereto, 1 equivalent (5.62 g, 39 mmol) of 3-methyl-2-oxobutanoic acid ethyl ester was added, followed by 1 eq. (6.24 g, 39 mmol) of bromine. Then, 1.5 ml of acetic acid was used for acidification. After decoloring the solution, the reaction was quenched using approx. 30 ml of sat. $NaHCO_3$ solution, and the mixture was transferred into a separating funnel. There, 100 ml diethyl ether and another 20 ml of NaHCO₃ were added. The aqueous layer was discarded, and the organic layer was re-extracted with 50 ml of NaHCO₃. The ether layer was washed with sat. NaCl solution and dried over sodium sulfate. The solvent was then removed on a rotary evaporator.

Yield: 6.94 g (79% of theory)

$^1$H NMR (400 MHz, $C_6D6$) δ ppm: 4.31 (q, 2 H, J=7.02 Hz); 1.95 (s, 6 H); 1.32 (t, 3 H, J=7.2 Hz).

GC-MS: 224.99[M+H]⁺, 143.07[M−Br]⁺, 122.93[M-CO-COOEt]⁺, 70.20[M−Br-COOEt]⁺.

Synthesis Example 2

Synthesis of 3-hydroxy-3-methyl-2-oxobutanoic Acid Ethyl Ester (6)

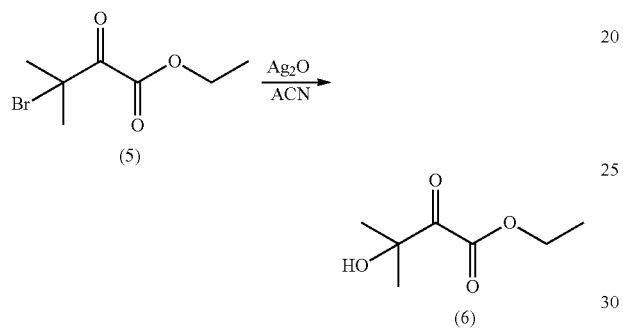

1 equivalent (4.46 g, 20 mmol) of 3-bromo-3-methyl-2-oxobutanoic acid ethyl ester was added to 0.5 eq. silver(I) oxide in 40 ml moist acetonitrile (ACN). The mixture was stirred for 12 hrs, and the light-grey precipitate was removed by filtration. The solution was then diluted using 100 ml of water and extracted with 200 ml of ether, and the organic layer was dried over sodium sulfate. After removing the solvent, the crude product was subjected to fractional distillation (120° C., 25 mbar).

Yield: 1.50 g (93% of theory)

$^1$H NMR (400 MHz, $C_6D_6$) δ ppm: 3.85 (q, 2H, J=7.31 Hz); 2.94 (bs, 1 H); 1.30 (s, 6H); 0.83 (t, 3H, J=7.09 Hz).

GC-MS: 161.16[M+H]⁺, 143.20[M—OH]⁺, 115.16[M—OEt]⁺, 87.09[M-COOEt]⁺, 59.06 [(CH₃)₂OH]⁺.

Synthesis Example 3

Synthesis of N,N'-dimethylamino Pyruvate (10)

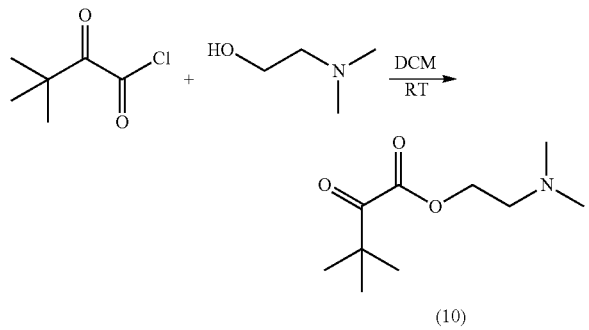

In a 100 ml three-necked round-bottom flask, 2,5 eq. N,N-dimethyl ethanolamine were added dropwise from a septum to a mixture of 1 eq. 3,3-dimethyl-2-oxobutanoyl chloride in 10 ml dichloromethane while cooling using an ice bath. After the addition had been completed, stirring was continued for 48 hrs at room temperature. After the reaction had been completed, the solvent was removed using a rotary evaporator. The product was obtained as a clear oil by Kugelrohr distillation at 1.2 mbar and 94° C.

Yield: 177 mg (17% of theory)

$^1$H NMR (400 MHz, $C_6D_6$, ppm): 4.11 (t, 2 H), 2.29 (t, 2H), 2.02 (s, 6 H), 1.16 (s, 9 H).

2.5 eq. N,N-dimethylethanolamine were added dropwise from a septum to a mixture of 1 eq. 3,3-dimethyl-2-oxobutanoyl chloride in 10 ml dichloromethane. After the addition had been completed, stirring was continued for 48 h at room temperature. After the reaction had been completed, the solvent was removed using a rotary evaporator. The product was obtained as a clear oil by Kugelrohr distillation at 1.2 mbar and 94° C.

Yield 177mg (17% of theory)

$^1$H NMR (400 MHz, $C_6D_6$, ppm): 4.11 (t, 2 H), 2.29 (t, 2H), 2.02 (s, 6 H), 1.16 (s, 9 H).

Synthesis Example 4

Synthesis of α-Ketoglutaric Acid Diethyl Ester (9)

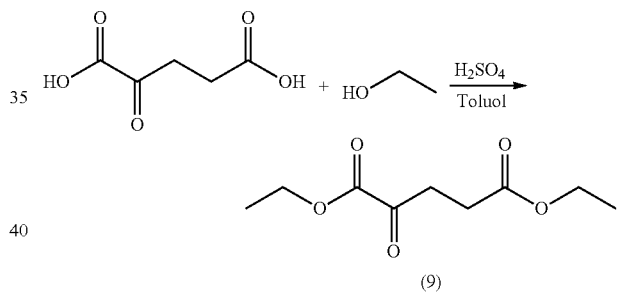

At first, α-ketoglutaric acid was re-crystallized from acetone. Subsequently, 1 eq. (3.662 g, 25 mmol) of α-ketoglutaric acid were weighed into a 250 ml three-necked round-bottom flask equipped with a condenser and a septum, followed by the addition of 100 ml of ethanol and 0.3 eq. (0.4 ml, 7.5 mmol) of sulfuric acid. The reaction mixture was magnetically stirred and refluxed. The oil bath was set to 100° C., and the reaction was left to proceed for 24 h. Reaction progress was monitores by thin-layer chromatography (PE:EE, 5:1; Rf 0.36). The solvent was evaporated using a rotary evaporator, followed by the addition of 50 ml of de-ionized water and neutralization of the solution using 1N KOH solution. The aqueous layer was extracted three times with 100 ml of ehtylacetate, and the combined organic layers were dried over Na₂SO₄. The solvent was then evaporated using a rotary evaporator. 4.193 g (83% of theory) crude yield were obtained. The crude product was chromatographically separated by means of MPLC using a 214 g silica column (PE:EE, 9:1). The product was detected using a UV detector (254 nm) and identified by DC (PE:EE, 5:1; Rf 0.36). The fractions containing the product were combined, and the solvent was evaporated using a rotary evaporator.

In total, 1.77 g (35% of theory) of α-ketoglutaric acid diethyl esther (9) were obtained as a colorless oil.

Rf: 0.36 (PE:EE, 5:1)

$^1$H NMR (400 MHz, CDCl$_3$, ppm): 4.32 (q, J=7.2 Hz, 2H), 4.13 (q, J=7.20 Hz, 2H), 3.14 (t, J=6.6 Hz, 2H), 2.65 (t, J=6.6 Hz, 2H), 1.36 (t, J=7 Hz, 3H), 1.24 (t, J=7 Hz, 3H).

$^{13}$C NMR (400 MHz, CDCl$_3$, ppm): 192.8, 172.0, 160.6, 62.6, 60.9, 34.2, 27.8, 14.2, 14.0.

GC-MS: 202.99 [M+H], 129.94 [M+H,—(CO—O—CH$_2$—CH$_3$)], 128.95 [M—(CO—O—CH$_2$—CH$_3$)], 101.99 [M+H,—(CO—CO—O—CH$_2$—CH$_3$)], 101.00 [M—CO—CO—O—CH$_2$—CH$_3$], 74.11 [M+H, —(CO—CH$_2$—CH$_2$—O—O—CH$_2$—CH$_3$)], 73.14 [M—(CO—CH$_2$—CH$_2$—O—O—CH$_2$—CH$_3$)], 55.13 [M+H,—(O—CH$_2$—CH$_3$),—(CH$_2$—CH$_2$—CO—O—CH$_2$—CH$_3$)].

Synthesis Example 5

Synthesis of α-Ketoglutaric Acid di-2-hydroxyethylmethacrylic Acid Ester (11)

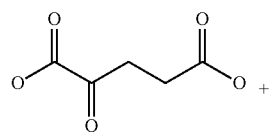

toglutaric acid, 2 eq. (7.290 g, 54 mmol) of 2-hydroxymethyl methacrylate, 0.7 wt % (78.5 mg) lipase (Candida antarctica) immobilized on acrylic resin (<5.000 U/g) and 565 ppm (10.1 mg) of 2,6-di-tert-butyl-4-methylphenol (BHT) were placed in a 50 ml single-necked round-bottom flask. The flask was equipped with a drying tube filled with calcium chloride. The mixture was magnetically stirred in an oil bath at 65° C. Reaction progress was monitored by NMR and TLC (PE:EE, 8:2; Rf 0.62), and after a reaction time of 140 hrs, the reaction was diluted with PE:EE (1:1) and chromatographically separated using a 90 g silica column by MPLC (PE:EE, 8:2). The combined product fractions were treated with BHT and evaporated using a rotary evaporator. 2.991 g (30% of theory) of the pure product were obtained as a colorless, transparent oil.

Rf: 0.62 (PE:EE, 8:2)

$^1$H NMR (400 MHz, (acetone-d$_6$, ppm): 6.05 (s, 2H, 2 CHH), 5.62-5.59 (m, 2H), 4.54-4.48 (m, 2H), 4.43-4.38 (m, 2H), 4.30 (s, 4H), 3.15 (t, J=6.6 Hz, 2H), 2.63 (t, J=6.6 Hz, 2H), 1.87 (t, J=1.2 Hz, 6H).

Synthesis Example 6

Synthesis of Ketoglutaric Acid-Hexanediol Polyester (12)

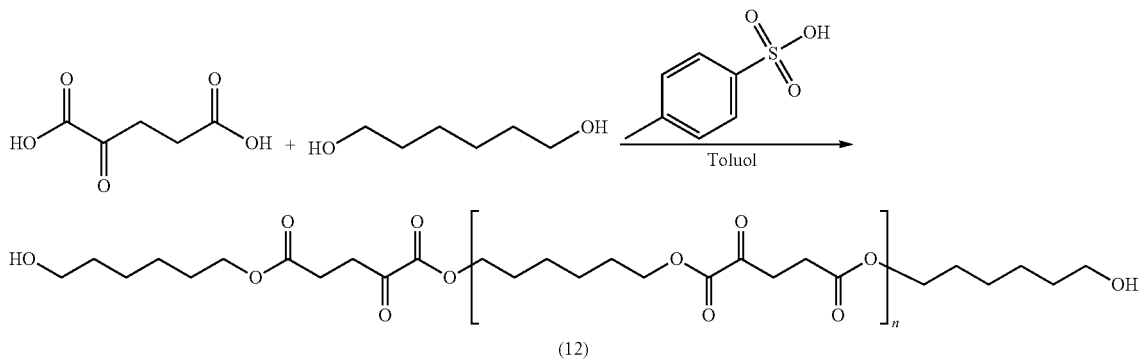

(12)

-continued

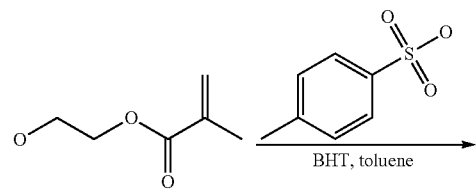

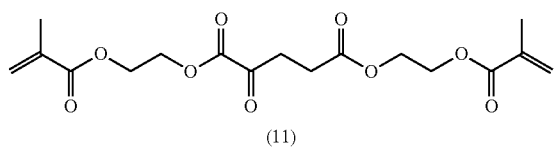

(11)

At first, α-ketoglutaric acid was re-crystallized from acetone. Subsequently, 1 eq. (3.943 g, 27 mmol) of α-ke- At first, α-ketoglutaric acid was re-crystallized from acetone and p-toluene sulfonic acid was re-crystallized from chloroform. Subsequently, 1 eq. (11.18 g, 80 mmol) of pure α-ketoglutaric acid, 1.01 eq. (9.54 g, 81mmol) 1,6-hexanediol and 0.0025 eq. (30.2 mg, 0.2 mmol) of pure p-toluene sulfonic acid were weighed into a 100 ml three-necked flask equipped with a magnetic stirrer and a Dean Stark trap. 30 ml abs. toluene were added, and the oil bath was heated to 125° C. Reaction progress was monitored by NMR, and the reaction was stopped after 24 hrs. The dissolved polyester was diluted with 30 ml abs. toluene and precipitated in 800 ml cold diethyl ether. The result obtained was a slightly yellow polyester that was dried in a vacuum drying oven at 50° C., followed by dissolution in 60 ml THF, filtering the solution and re-precipitation in 800 ml cold diethyl ether. After drying under vacuum, 11.36 g (62%) of the polyester were obtained as a white polymer.

Molecular weight, Mn (by GPC and NMR)≈10,000; n≈40

$^1$H NMR (400 MHz, CDCl$_3$, ppm): 4.26 (t, J$_{HH}$=6.6 Hz, 40 H), 4.08 (t, J$_{HH}$=6.6 Hz, 40 H), 3.65 (t, J$_{HH}$=6.6 Hz, 4H), 3.15 (t, $J_{HH}$=6.6 Hz, 40H), 2.67 (t, $J_{HH}$=6.6 Hz, 40H), 1.78-1.72 (m, 40H), 1.68-1.60 (m, 40H), 1.45-1.36 (m, 80H).

Synthesis Example 7

Synthesis of α-Ketoglutaric Acid-1,6-hexanediol Polyester Having 2-isocyanatoethyl-methacrylate-modified Terminal Groups (13)

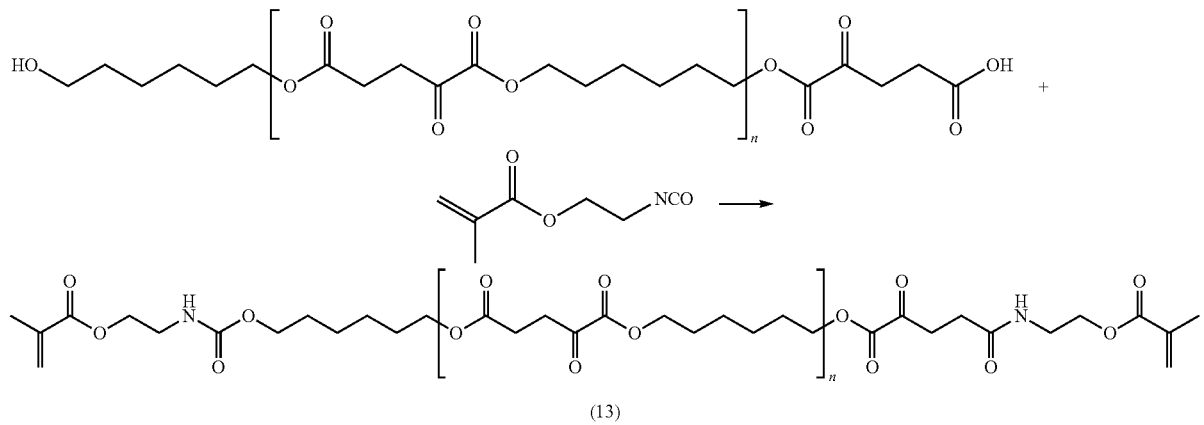

(13)

In a first step, 1 eq. of the polyester (0.98 g, 0.2 mmol), 2 drops dibutyltin dilaurate as a catalyst and 20 ml of abs. toluene were charged into a 50 ml three-necked round-bottom flask. The flask was flushed with argon and equipped with a septum and an argon balloon. Subsequently, 2.05 eq. (0.6 ml, 0.4 mmol) of 2-isocyanatoethylmeth-acrylate were added dropwise via the septum. The mixture was stirred for 14 hrs at room temperature and then quenched using 5 ml of methanol. 20 ml of distilled acetone were added, and the polyester was precipitated in 300 ml of cold diethyl ether, yielding a white polymer (0.36 g, 34% of theory).
Molecular weight, Mn (by GPC and NMR)≈10,000; n≈40
$^1$H NMR (400 MHz, CDCl$_3$, ppm): 6.12 (s, 2H), 5.59 (s, 2H), 5.342 (s, 2H), 4.26 (t, $J_{HH}$=6.6 Hz, 80 H), 4.15 (t, 4H, $J_{HH}$=6.4 Hz), 4.08 (t, $J_{HH}$=6.6 Hz, 80 H), 3.65 (t, $J_{HH}$=6.4 Hz, 4H), 3.15 (t, $J_{HH}$=6.6 Hz, 80H), 2.67 (t, $J_{HH}$=6.6 Hz, 80H), 1.95 (s, 3H) 1.78-1.72 (m, 80H), 1.68-1.60 (m, 80H), 1.45-1.36 (m, 160H).

In the following examples, of the inventive use of compounds of formula (I) as photo-initiators, reaction mixtures containing the respective photoinitiator, the specified liquid monomer and optionally a specified co-intiator were produced and cured for 10 min under a nitrogen atmosphere by exposure to an OmniCure® S2000 mercury lamp having a wave length filter of 320 to 500 nm and an UV light intensity of 1 W/cm$^2$, while the progress of the reactions was monitored by photo-DSC type NETSCH DSC 204 F1 Phoenix.

All measurements were carried out at least twice, the respective tables showing the average values for the respective initiators.

In the tables, $R_P$ represents the polymerization rate and is thus an indicator of the reactivity of a system. A high value means that many monomer groups are reacted at the same time and that the curing process is generally shorter. $t_{max}$ is the time (in s) it takes until maximum heat development is reached and is thus an indicator of how long it takes to reach the gelling point and thus a certain initial solidity. Short times are thus more desirable. t95% is the time (in s) after which 95% of the entire reaction heat have been released and is thus an indicator of the rate at which a reaction occurs, lower values again being advantageous. DBC is the double bond conversion rate calculated based on the reaction heat released during polymerization (in J per g) of the respective formulation. For the conversion rate, it is desirable to achieve values that are as high as possible.

In all experiments, acrylates and methacrylates that are typically used in the field of coating were used as monomers.

In all formulations, the respective photoinitiator was used in an equimolar amount with respect to 1 wt % of ethyl pyruvate (1), which was the initiator having the lowest molecular weight, and weighed in accordingly, and co-initiators, if contained, were weighed in equimolar amounts with respect to the respective initiator. Subsequently, 12±0.5 mg of the reaction mixtures were weighed into DSC aluminum pans, and the pans were covered with cover glasses.

Examples 1 to 5, Comparative Example 1—Type II Initiators

In this group of experiments, the hydrogen abstractors of the Examples 1 to 4 (E1 to E4) and one Comparative Example (C1) were tested in combination with a co-initiator serving as a hydrogen donor.

Initiators

Example 1

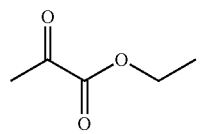

(1)

Example 2

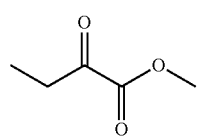

(2)

Example 3

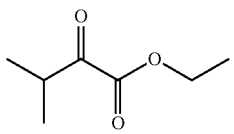
(3)

Example 4

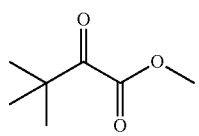
(4)

Example 5

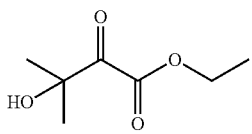
(6)

Comparative Example 1

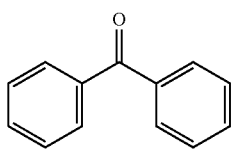
(BP)

Monomer

Hexanediol Diacrylate (HDDA)

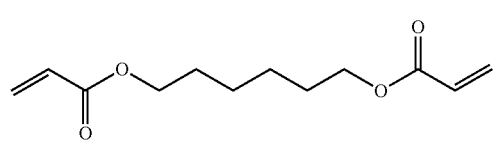
HDDA

Co-Initiator 4-dimethylaminobenzoic Acid Ethyl Ester (DMAB)

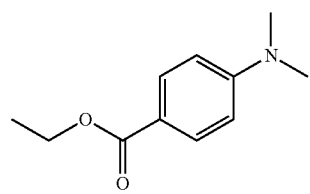
DMAB

Results:

TABLE 1

| | $R_P$ [mmol·l$^{-1}$·s$^{-1}$] | $t_{max}$ [s] | $t_{95\%}$ [s] | DBC [%] |
|---|---|---|---|---|
| C1 | 96 | 10.1 | 85.5 | 68.9 |
| E1 | 230 | 7.7 | 41.7 | 66.5 |
| E2 | 204 | 8.5 | 40.5 | 60.9 |
| E3 | 241 | 7.5 | 36.6 | 65.8 |
| E4 | 170 | 10.6 | 42.5 | 59.1 |
| E5 | 218 | 6.0 | 73.0 | 63.1 |

Table 1 shows that the novel α-ketoesters according to the present invention achieve surprisingly high polymerization rates when compared to benzophenone (BP), the industrial reference. This is mainly shown by the fact that the time until 95% of the overall conversion is reached ($t_{95}\%$) is significantly shorter. The final conversion (DBC) remains at a level comparable to that using the industrial BP/DMAB system. In particular, the compounds of Examples 1 to 3 are distinguished by their high reactivity and a particularly high conversion rate, among which compounds, methylethyl-oxobutanoate (3) of Example 3 achieved outstanding values.

Examples 6 and 7, Comparative Example 2—Type II Initiators

Two of the above experiments were repeated using the same two initiators and BP as a Comparative Example, using a non-aromatic co-initiator (MDEA) instead of the aromatic amine (DMAB).

Initiators

Example 6

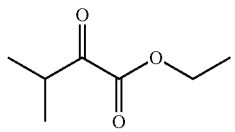
(3)

Example 7

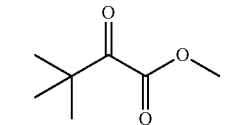
(4)

Comparative Example 2

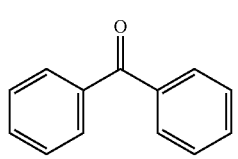
(BP)

Monomer

Hexanediol Diacrylate (HDDA)

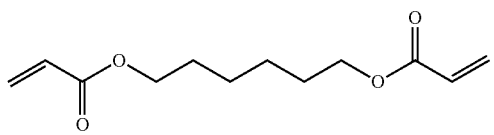
HDDA

Co-Initiator

Methyldiethanolamine (MDEA)

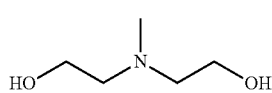
MDEA

Results

TABLE 2

|  | $R_P$ [mmol · l$^{-1}$ · s$^{-1}$] | $t_{max}$ [s] | $t_{95\%}$ [s] | DBC [%] |
|---|---|---|---|---|
| C2 | 109 | 10.8 | 77.0 | 69.3 |
| E6 | 228 | 6.7 | 56.5 | 65.2 |
| E7 | 234 | 7.7 | 41.0 | 64.6 |

It was also possible to achieve good results using the non-aromatic co-initiator with the compounds (3) and (4). The two ketoesters showed a significantly higher reactivity and zo lower t95% than the reference system.

Examples 8 and 9, Comparative Example 3—Type II Initiators

The compounds (1) and (4) were compared to the commercial initiator ethylphenyl glyoxylate (PGO).

Initiators

Example 8

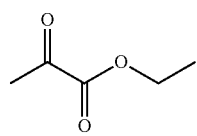
(1)

Example 9

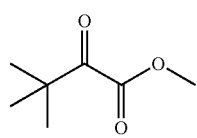
(4)

Comparative Example 3

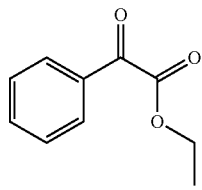
(PGO)

Comparative Example 4 Comparative Example 5

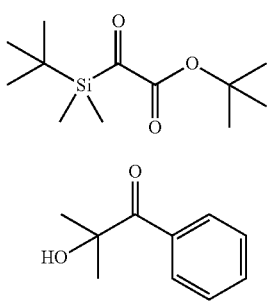
(SiKE)

(DC)

Monomer

Hexanediol Diacrylate (HDDA)

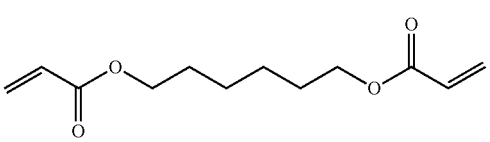
HDDA

Results

TABLE 3

|  | $R_P$ [mmol · l$^{-1}$ · s$^{-1}$] | $t_{max}$ [s] | $t_{95\%}$ [s] | DBC [%] |
|---|---|---|---|---|
| C3 | 204 | 14.1 | 63.0 | 75.1 |
| E8 | 210 | 8.5 | 56.0 | 69.3 |
| E9 | 214 | 8.3 | 53.5 | 64.6 |

Surprisingly, the novel compounds (1) (Example 8) and (4) (Example 9) achieved significantly higher polymerization rates than the known phenyl glyoxylate initiator (PGO) (Comparative Example 3). The maximum polymerization rate was reached in almost half the time. The final conversion was also achieved up to 10 s earlier when using the novel α-ketoesters.

Example 10—Type II Initiator

The compound that had achieved the best results in the experiments so far, compound (3), was tested using thiol as a co-initiator; the achieved results were compared to those of Example 3 where DMAB had been used as a co-initiator.

Initiator

Example 10

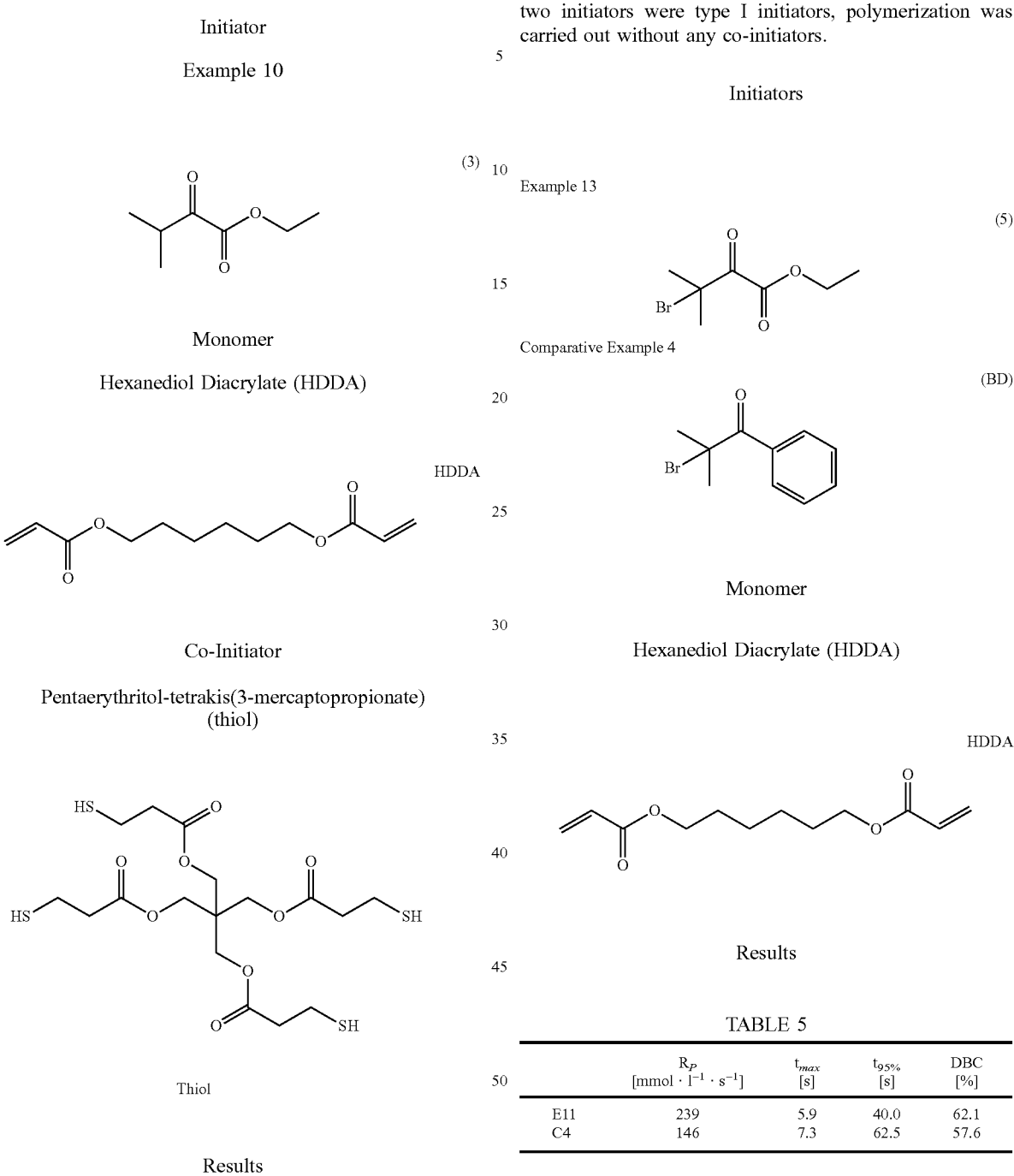

Monomer

Hexanediol Diacrylate (HDDA)

Co-Initiator

Pentaerythritol-tetrakis(3-mercaptopropionate) (thiol)

Thiol

Results

TABLE 4

| | $R_P$ [mmol · l$^{-1}$ · s$^{-1}$] | $t_{max}$ [s] | $t_{95\%}$ [s] | DBC [%] |
|---|---|---|---|---|
| E3 | 241.0 | 7.5 | 36.6 | 65.8 |
| E10 | 233.5 | 8.0 | 45.0 | 68.0 |

It can be seen that also the thiol is very well suited for use as a co-initiator for type II α-ketoester initiators.

Example 11, Comparative Example 4—Type I initiators

In this experiment, the brominated ketoester (5) from Synthesis Example 1 was compared to a known initiator that also contained bromide, "bromo darocur" (BD). As these two initiators were type I initiators, polymerization was carried out without any co-initiators.

Initiators

Example 13

Comparative Example 4

Monomer

Hexanediol Diacrylate (HDDA)

Results

TABLE 5

| | $R_P$ [mmol · l$^{-1}$ · s$^{-1}$] | $t_{max}$ [s] | $t_{95\%}$ [s] | DBC [%] |
|---|---|---|---|---|
| E11 | 239 | 5.9 | 40.0 | 62.1 |
| C4 | 146 | 7.3 | 62.5 | 57.6 |

The use of the novel α-ketoester (5) according to the invention provided clearly better results than the common bromide-containing type I initiator according to the state of the art, the novel compound (5) surprisingly even achieving significantly better reactivity results than the latter.

Examples 12 to 15, Comparative Example 5—Type II initiators

In this group of experiments, the experiments from Examples 1 to 4 and Comparative Example 1 were repeated, using a di-methacrylate mixture from the field of dental engineering as a monomer instead of the diacrylate that had been used above.

Initiators
Example 12
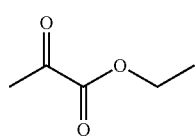
Example 13
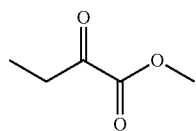
Example 14
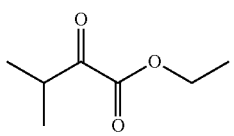
Example 15
(1)
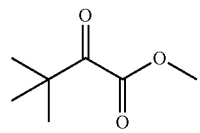
(2)
(3)
(4)
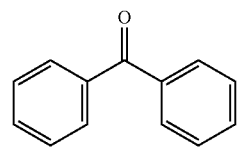
Comparative Example 5
(BP)
Monomers
Dental Dimethacrylate Mixture (DDM)
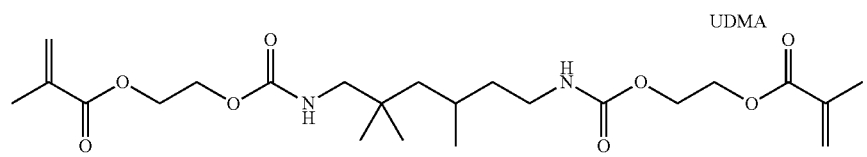
UDMA
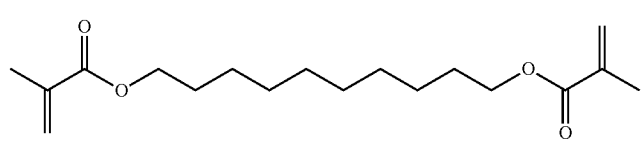
D3MA
1 eq. UDMA/1 eq. D3MA DDM Co-Initiator 4-dimethylaminobenzoic Acid Ethyl Ester (DMAB)

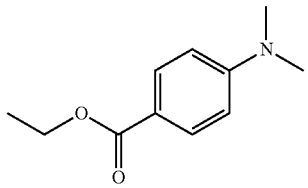

DMAB

Results

TABLE 7

|  | $R_P$ [mmol·l$^{-1}$·s$^{-1}$] | $t_{max}$ [s] | $t_{95\%}$ [s] | DBC [%] |
| --- | --- | --- | --- | --- |
| C5 | 21.4 | 18.5 | 146.5 | 50 |
| E12 | 74.5 | 11.9 | 83.0 | 57 |
| E13 | 71.2 | 12.2 | 85.5 | 57 |
| E14 | 81.5 | 11.0 | 58.5 | 57 |
| E15 | 55.9 | 14.9 | 69.5 | 51 |

It becomes clear that the methacrylate monomer can also be cured more efficiently using α-ketoesters as initiators than when using benzophenone. The reactivity of the ketoesters (1) to (4) of the invention is surprisingly several times—up to 2.5 times—higher higher than that of benzophenone, and the time until the peak maximum is reached is much shorter than in the Comparative Example. In Examples 12 to 15 of the invention, the double bond conversion was much higher using the methacrylate monomer than when using the reference initiator, and maximum conversion was even reached 2 to 3 times faster, which further underlines that the present invention is superior to the state of the art.

Example 16, Comparative Example 6—Type II Initiators

In this Example, a ketoester, compound (1), was directly compared by means of photo-DSC measurements to benzophenone (BP) as a known type II initiator when it comes to curing a known difunctional vinyl ester, i.e. divinyl adipate (DVA), that was used as a monomer.

Initiators

Example 16

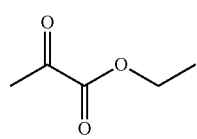

(1)

Comparative Example 6

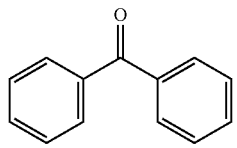

(BP)

Monomer

Divinyl Adipate (DVA)

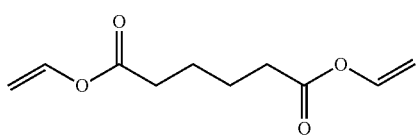

DVA

Co-Initiator 4-dimethylamino Benzoic Acid Ethyl Ester (DMAB)

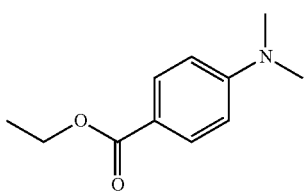

DMAB

Results

TABLE 8

|  | DSC [mW·mg$^{-1}$] | $t_{max}$ [s] | Area [J·g$^{-1}$] |
| --- | --- | --- | --- |
| E16 | 1.7 | 194 | 466 |
| C6 | 4.37 | 55 | 642 |

It becomes evident that, when using the vinyl ester monomer DVA that is rather unreactive when compared to (meth)acrylates, the ketoester (1) according to the present invention achieves clearly worse results than benzophenone in the Comparative Example. This comparison, however, still shows that it is generally possible to cure biocompatible monomers such as DVA using food-safe α-ketoesters. As benzophenone and other commercially available initiators may be harmful to health, the advantage of their usability in this context will offset the lower reactivity of vinyl esters.

Examples 17 and 18, Comparative Example 7—Type II initiators in hydrogels

Using the partially water-soluble ketoesters in a hydrogel formulation with PEG700DA (polyethylene glycol diacrylate with Mn 700) and 50 wt % water for polymerizing hydrogels worked surprisingly well. PBQ was used as a commercially available reference initiator, with MDEA as a co-initiator. The ketoesters ethyl pyruvate (1) and dimethylfurandione (8) can be used as novel initiators without any co-initiator. Due to its longwave absorption maximum ($\lambda_{max}$=378 nm instead of 330 nm for compound (1)), compound (8) can also be used using visible light which is harmless for cells.

Initiators

Example 17

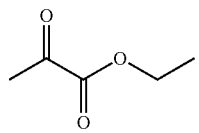
(1)

Example 18

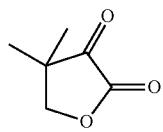
(8)

Comparative Example 7

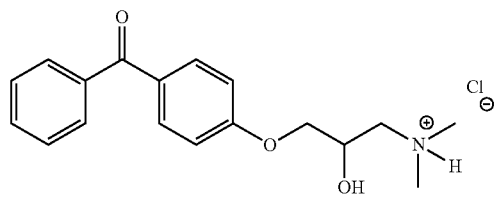
(BPQ)

Monomer

Polyethylene Glycol (700) Diacrylate

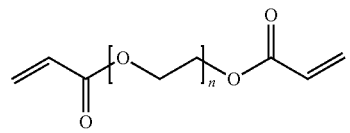

PEG(700)DA
Mn = 700 g/mol

Co-Initiator

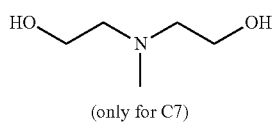
MDEA (only for C7)

Results

TABLE 9

|  | $R_P$ [mmol·l$^{-1}$·s$^{-1}$] | $t_{max}$ [s] | $t_{95\%}$ [s] | DBC [%] |
|---|---|---|---|---|
| C7 | 30 | 8.8 | 87 | 50 |
| E17* | 33 | 8.5 | 83 | 48 |
| E18* | 26 | 10.3 | 78 | 56 |

*without co-initiator

As becomes clear from Table 9, the biocompatible initiators of the invention proved surprisingly reactive and achieved results that were comparable to those achieved using the commercial initiator. In this connection, it has to be stated that in a study using the mouse fibroblast cell line L929 and the commercial compound BPQ, significant toxic effects were already observed at a concentration of 8 mmol/l, while the compounds (1) and (8) did not show any cytotoxicity even at concentrations that were twice as high. This may constitute an additional advantage for biological applications in which hydrogels are commonly used.

Examples 19 and 20, Comparative Examples 8 and 9—Type II initiators Surprisingly, the biocompatible compound (8) from Example 18 was equally soluble in aqueous and non-aqueous monomer systems. For this reason, reactivity was tested in acrylates (Example 19) and methacrylates (Example 20); in the latter case, DMAB was additionally used as co-initiator because of the low reactivity of the methacrylates. The new system was compared with the industrial standard initiator benzophenone (BP) in acrylates (Comparative Example 8) and methacrylates (Comparative Example 9).

Initiators

Examples 19 and 20

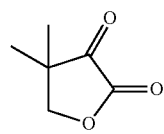
(8)

Comparative Examples 8 and 9

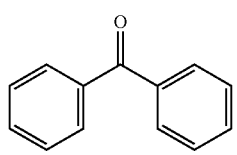
(BP)

Monomers

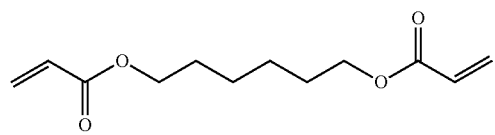

Hexanediol diacrylate (HDDA) (E19 and C8)

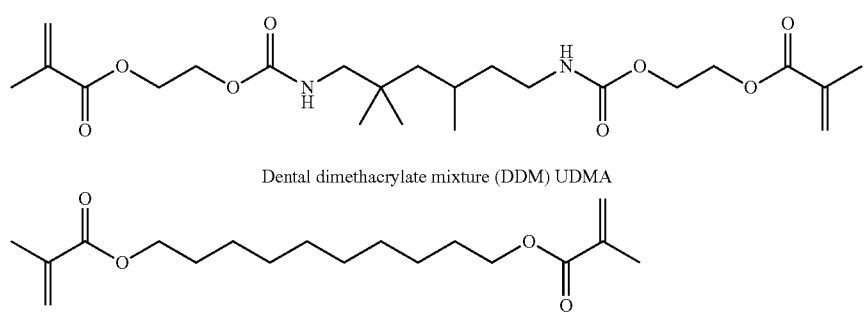

Dental dimethacrylate mixture (DDM) UDMA (E20 and C9)

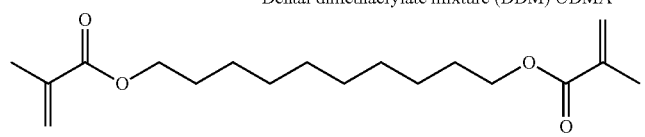

D3MA
1 eq. UDMA/1eq. D3MA DDM

Co-Initiator
(E20, C8 and C9)

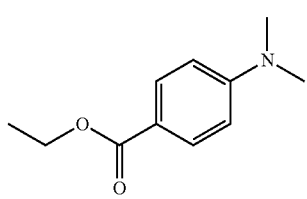

DMAB

Results

TABLE 10

| | $R_P$ [mmol·l⁻¹·s⁻¹] | $t_{max}$ [s] | $t_{95\%}$ [s] | DBC [%] |
|---|---|---|---|---|
| C8 | 93 | 11.1 | 69 | 69 |
| C9 | 21 | 18.2 | 143 | 49 |
| E19 | 189 | 11.6 | 58 | 66 |
| E20 | 52 | 18.2 | 90 | 54 |

As can be seen in table 10, the reactivity of compound (8) of the invention without any co-initiator in HDDA (Example 19) was surprisingly more than twice as high as that of the reference BP without co-initiator (Comparative Example 8). A comparable final conversion is also achieved more rapidly. In methacrylates, the use of DMAB as a co-initiator (Example 20) of compound (8) yields not only a polymerization rate that is more than twice as high, but, at the same time, also a significantly higher final conversion much more rapidly than in the reference example (Comparative Example 9).

Example 21 and 22, Comparative Example 10—Type II Initiators

Ketoglutaric acid was esterified with simple alcohols (Exmaple 21) and hydroxyethyl methacrylate (HEMA) Example 22) to produce polymerizable initiators, and their reactivity was tested in the di-acrylate HDDA. Reactivity was again compared to that of a benzophenone/amine system (Comparative Example 10).

Initiators

Example 21

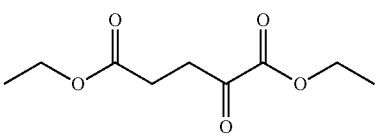
(9)

Comparative Example 10

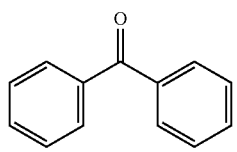
(BP)

Example 22

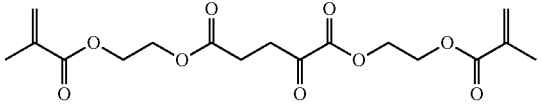
(11)

Monomer

Hexanediol Diacrylate (HDDA)

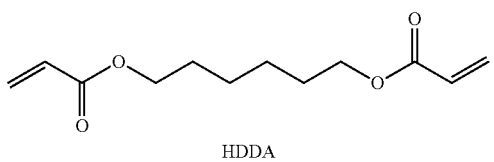 [SMILES: C=CC(=O)OCCCCCCOC(=O)C=C ; "HDDA"]

HDDA

Co-Initiator

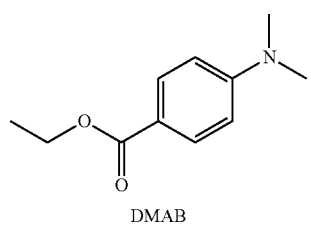

DMAB

Results

TABLE 11

| | $R_P$ [mmol·l⁻¹·s⁻¹] | $t_{max}$ [s] | $t_{95\%}$ [s] | DBC [%] |
|---|---|---|---|---|
| C10 | 93 | 11.1 | 69 | 69 |
| E21 | 201 | 9.2 | 58 | 67 |
| E22 | 203 | 11.6 | 53 | 64 |

Surprisingly, the polymerization rate of these α-ketoesters was also at least twice as high as that of the BP/amine reference system in Comparative Example 10. A high final conversion is also achieved more rapidly. Additionally, the polymerizable groups of compound (11) make sure that any residual initiator will not be able to diffuse from the polymer after polymerization, which is particularly important for applications in the fields of medicine and food.

Examples 23 and 24 and Comparative Example 11—Type II initiators α-Ketoglutaric acid esters can also be used for methacrylates. For this reason, substances (9) and (11) were tested in comparison with benzophenone (BP) in the dental formulation DDM, using DMAB as a co-initiator.

Initiators

Example 23

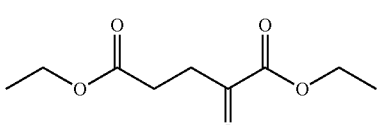 (9)

Comparative Example 11

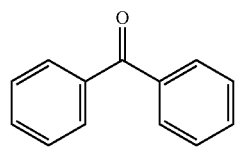 (BP)

Example 24

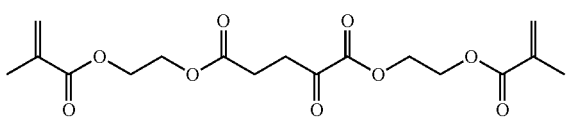 (11)

Monomers

Dental Dimethacrylate Mixture (DDM)

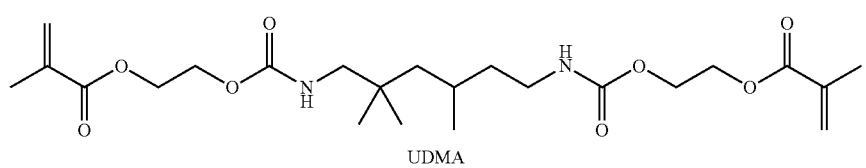

UDMA

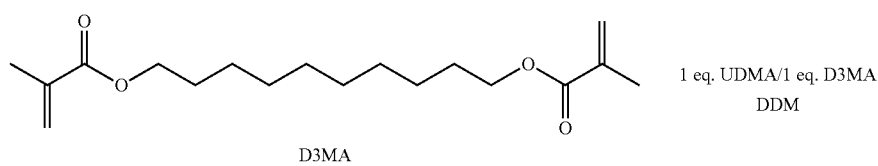

D3MA 1 eq. UDMA/1 eq. D3MA
DDM

Co-Initiator

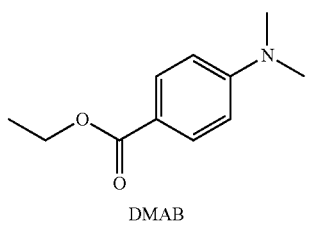

DMAB

Results

TABLE 12

| | $R_P$ [mmol*l$^{-1}$*s$^{-1}$] | $t_{max}$ [s] | $t_{95\%}$ [s] | DBC [%] |
|---|---|---|---|---|
| C11 | 21 | 18.2 | 143 | 49 |
| E23 | 66 | 14.3 | 85 | 53 |
| E24 | 57 | 14.5 | 93 | 52 |

Surprisingly, the polymerization rate achieved in unreactive methacrylates using the novel α-ketoglutaric acid esters and DMAB as a co-initiator was 3 times as high as that of the reference system, as can be seen from table 12. Polymerization proceeds much more rapidly than in case of the reference substance BP and results more rapidly in higher final conversion rates.

Example 25, Comparative Example 12—Polymeric Type II Initiators

As α-ketoglutaric acid is a dicarboxylic acid, it was also possible to produce polyesters from hexanediol and α-ketoglutaric acid. Polymeric initiators have the advantage that they do not migrate from the resulting polymer, which is why they are used in the fields of food and medicine. Additionally, polyesters can be modified in various ways, so that their solubility, functionality, and degradability can be adapted to specific applications.

Initiators

Example 25

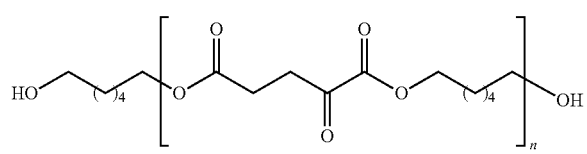

(12)

Comparative Example 12

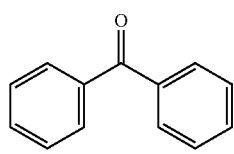

(BP)

Monomer

Hexanediol Diacrylate (HDDA)

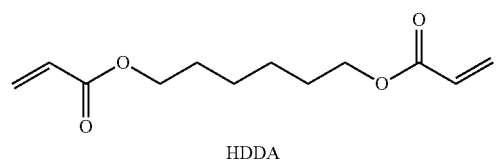 [SMILES: C=CC(=O)OCCCCCCOC(=O)C=C ; "HDDA"]

HDDA

Co-Initiator

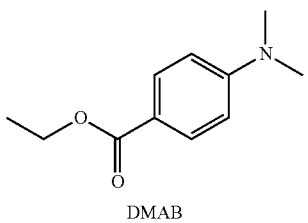

DMAB

Results

TABLE 13

| | $R_P$ [mmol · l$^{-1}$ · s$^{-1}$] | $t_{max}$ [s] | $t_{95\%}$ [s] | DBC [%] |
|---|---|---|---|---|
| C12 | 93 | 11.1 | 69 | 69 |
| E25 | 144 | 9.2 | 71 | 64 |

As illustrated in table 13, the polyester (12) of Example 25 shows an unexpectedly high reactivity when compared to benzophenone (BP) in Comparative Example 12. In spite of its high molecular weight and the associated slow diffusion, the polymerization rate is more than one third higher. α-Ketoglutaric acid polyesters are known for their biocompatibility and their biodegradability. The use of this class of substances as photoinitiators is, however, completely new, and the high polymerization rates were very surprising.

Example 26—Type II Initiator, Curing Test

Amines are used as co-initiators to increase the reactivity of type II initiators. It is also possible to bind the co-initiator covalently to the initiator in order to avoid two-component systems. Compound (10) is such an initiator that was tested using hexanediol diacrylate (HDDA) as a monomer in the present example.

Initiator

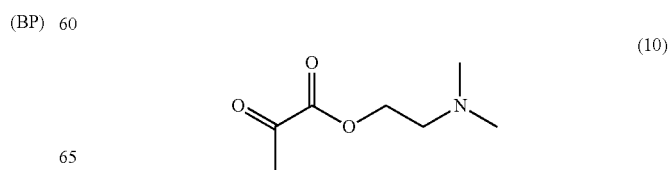

(10)

Monomer

Hexanediol Diacrylate (HDDA)

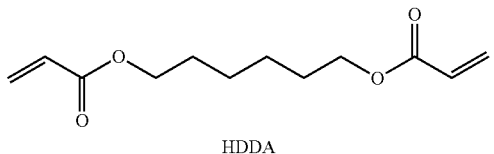 [SMILES: C=CC(=O)OCCCCCCOC(=O)C=C ; "HDDA"]

HDDA 1 g of a mixture of HDDA and 1 wt % of compound (10) were irradiated in a silicone mold placed in an Intelli-Ray 400 W UV oven at 100% power. After a few seconds, a transparent, hard sample rod was obtained, proving the suitability of the present invention for synthesizing molded articles.

Example 27—Polymeric Type II Initiator, Curing Test

Undesired migration of unreacted initiator molecules or their degradation products during irradiation constitutes a major proble, in particular in the fields of food and medicine. This is why macromolecular initiators and, in particular, macromolecular initiators having polymerizable terminal groups are of great interest. Its high molecular weight and reactive terminal groups prevent the initiator from diffusing out of the resulting polymer. In this connection, compound (13) was examined using hexanediol diacrylate (HDDA) as a monomer.

Initiator

Example 27

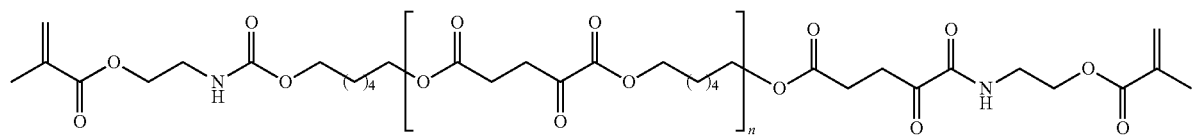

Monomer

Hexanediol Diacrylate (HDDA)

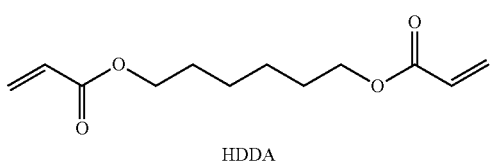 [SMILES: C=CC(=O)OCCCCCCOC(=O)C=C ; "HDDA"]

HDDA 1 g of a mixture of HDDA and 1 wt % of compound (13) was exposed in a silicone mold in an Intelli-Ray 400 W UV oven at 100% power. After a few seconds, a clear, hard sample rod was obtained, which proved that the polymeric initiator according to the present invention was suitable for synthesizing molded articles.

The above examples clearly show that, depending on the specific reaction conditions, the use of α-ketoesters provides a number of advantages compared to known initiators, so that the present invention constitutes a valuable addition to the state of the art.

The invention claimed is:
1. A photoinitiator or photosensitizer of the following formula (I) for use in a photopolymerizable composition:

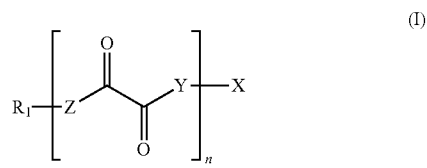

wherein
$R_1$ represents a monovalent, linear, branched or cyclic, aliphatic hydrocarbon group having 1 to 20 carbon atoms, which is optionally substituted with one or more substituents selected from —Cl, —Br, —OH, =O, —NH—CO—OR$_2$, —NH—CO—R$_2$ or free-radically or ionically polymerizable groups, wherein each $R_2$ radical is independently selected from —H or $C_{1-6}$ alkyl;
n is ≥1, wherein
  i) if n=1, Z and Y are not present and X represents —OR$_3$; and
  ii) if n is >1, Z represents —OR$_4$—, Y represents —OR$_5$— and X represents —H or —OH;
wherein
  $R_3$ represents —H or one of the options mentioned for $R_1$; and
  $R_4$ and $R_5$ each independently represent a bivalent hydrocarbon group for which otherwise the same options as mentioned for $R_1$ apply;
wherein the polymerizable moieties as optional substituents of $R_1$ are selected from polymerizable double or triple bonds as well as lactam, lactone and epoxide moieties, which are subjectable to ring-opening polymerization;
and wherein any two of $R_1$ to $R_5$ may be optionally linked to one another to form a ring or a dimer;
wherein the compound of formula (I) is used in photopolymerizable compositions as a photoinitiator in combination with one or more co-initiators comprising one or more mono- or polyhydric alcohols selected from sugars, glycerol, thiols, polyethylene glycol and polypropylene glycol; and/or wherein the compound of formula (I) is used in a photoinitiator or photosensitizer composition to be cured inside the human body or in curable compositions from the food sector.

2. The photoinitiator or photosensitizer according to claim 1, wherein, in formula (I):
  a) $R_1$ represents a linear, branched or cyclic aliphatic hydrocarbon group having 1 to 20 carbon atoms, in which one or more carbon atoms may have been replaced by oxygen atoms and which is optionally substituted with one or more substituents selected from —Cl, —Br, —OH and —SH; and/or
  b1) n=1 and X represents —$OR_3$, wherein $R_3$ independently represents —H or one of the options described for $R_1$; or
  b2) n is >1 and is selected from the range from 2 to 100 or from 2 to 50 or from 2 to 20, Z represents —$OR_4$—, Y represents —$OR_5$— and X represents —OH.

3. The photoinitiator or photosensitizer according to claim 1, wherein the compound of formula (I) is used as a type I or type II photoinitiator.

4. The photoinitiator or photosensitizer according to claim 1, wherein the compound of formula (I) is used in photopolymerizable compositions as a photoinitiator in combination with one or more co-initiators.

5. The photoinitiator or photosensitizer according to claim 4, wherein the one or more compounds is/are used as co-initiator/s further comprise(s) a compound selected from amines (—NR—), silanes (≡SiH—), germanes (≡GeH—), phosphines (—PRR'R"—), ethers (>CH—O—CH<), iodonium (—I⁺—) and sulfonium (≡S⁺—) salts and compounds based on derivatives thereof.

6. The photoinitiator or photosensitizer according to claim 1, wherein the compound of formula (I) is used in an amount of 0.1 to 10 parts by weight per 100 parts by weight of polymerizable monomers.

7. The photoinitiator or photosensitizer according to claim 1, wherein the compound of formula (I) is used for curing acrylate or methacrylate monomers.

8. A photopolymerizable composition comprising at least one compound of formula (I) as a photoinitiator or photosensitizer, at least one photopolymerizable monomer,

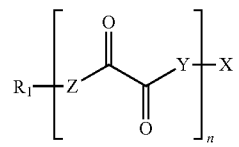

wherein in formula (I):
  $R_1$ represents a monovalent, linear, branched or cyclic, aliphatic hydrocarbon group having 1 to 20 carbon atoms, which is optionally substituted with one or more substituents selected from —Cl, —Br, —OH, =O, —NH—CO—$OR_2$, —NH—CO—$R_2$ or free-radically or ionically polymerizable groups, wherein each $R_2$ radical is independently selected from —H or $C_{1-6}$ alkyl;
  n is ≥1, wherein
  i) if n =1, Z and Y are not present and X represents —$OR_3$; and
  ii) if n is >1, Z represents —$OR_4$—, Y represents —$OR_5$— and X represents —H or —OH;
wherein
  $R_3$ represents —H or one of the options mentioned for $R_1$; and
  $R_4$ and $R_5$ each independently represent a bivalent hydrocarbon group for which otherwise the same options as mentioned for $R_1$ apply;
wherein the polymerizable moieties as optional substituents of Ri are selected from polymerizable double or triple bonds as well as lactam, lactone and epoxide moieties, which are subjectable to ring-opening polymerization;
wherein any two of $R_1$ to $R_5$ may be optionally linked to one another to form a ring or a dimer;
wherein the photopolymerizable composition additionally comprises one or more co-initiators comprising mono- or polyhydric alcohols selected from sugars, glycerol, thiols, polyethylene glycol and polypropylene glycol; and/or
wherein the photopolymerizable composition is to be cured inside the human body or in curable compositions from the food sector.

* * * * *